United States Patent [19]

Milana

[11] 4,448,527
[45] May 15, 1984

[54] METHOD AND APPARATUS FOR DETECTING SURFACE DEFECTS IN MECHANICAL WORKPIECES

[75] Inventor: Emilio Milana, Rivalta, Italy

[73] Assignee: Centro Ricerche Fiat S.p.A., Orbassano, Italy

[21] Appl. No.: 346,672

[22] Filed: Feb. 8, 1982

[51] Int. Cl.$^3$ .............................................. G01N 21/00
[52] U.S. Cl. .................................. 356/237; 250/225; 350/374
[58] Field of Search ............... 356/364, 365, 366, 368, 356/370, 237; 250/225; 350/374, 384, 393; 358/106, 232; 365/121

[56] References Cited

U.S. PATENT DOCUMENTS 4,283,145  8/1981  Miyazawa ........................... 356/364

FOREIGN PATENT DOCUMENTS 52-24554  2/1977  Japan ................................... 356/237

OTHER PUBLICATIONS

Nisenson et al., "Real Time Optical Processing with Bi$_{12}$SiO$_{20}$ PROM", *Applied Optics*, vol. 11, No. 12, pp. 2760–2766.

Iwasa, "Optical Processing: A Near Real-Time Coherent System Using Two Itek PROM Devices", *Applied Optics*, vol. 15, No. 6, pp. 1418–1424.

*Primary Examiner*—William L. Sikes
*Assistant Examiner*—Matthew W. Koren
*Attorney, Agent, or Firm*—Sughrue, Mion, Zinn, Macpeak and Seas

[57] ABSTRACT

The detection of surface defects in mechanical parts is effected by the analysis of diffracted light coming from these defects. The detection method includes the steps of illuminating the surface of the part to be examined with incoherent light and forming a flat image of the said surface in a transparent photosensitive layer of a spatial light modulator. The spatial distribution of the intensity of the incoherent light reflected by the said surface produces a corresponding and proportional spatial distribution of values of refractive index in the photosensitive layer. This layer is illuminated with plane polarized, coherent light by frame scanning in elementary areas. During the scanning operation, the variations in at least one of the polarization components of the coherent light are detected by a matrix of converters after the light has traversed the said transparent photosensitive medium.

11 Claims, 2 Drawing Figures

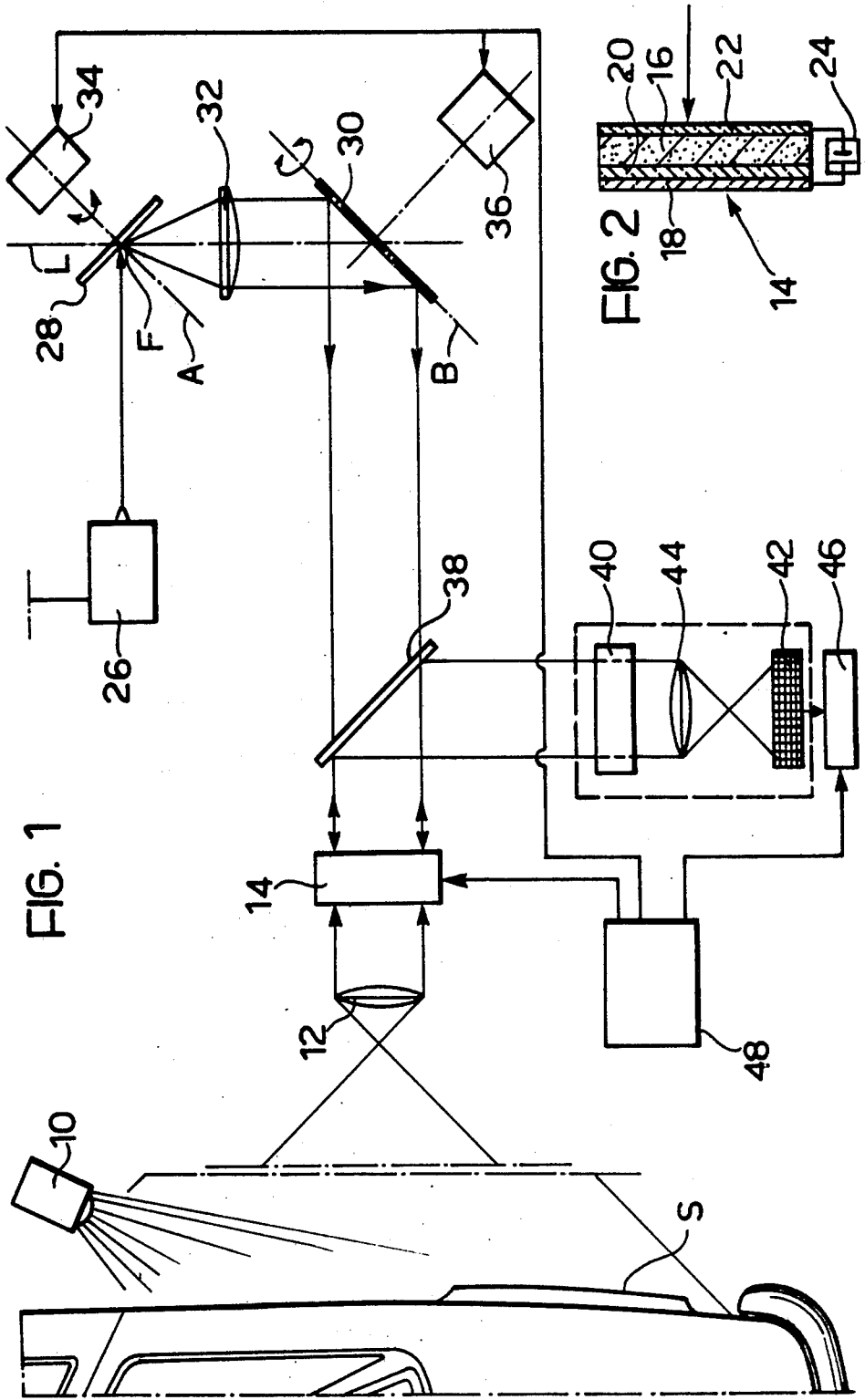

METHOD AND APPARATUS FOR DETECTING SURFACE DEFECTS IN MECHANICAL WORKPIECES

FIELD OF THE INVENTION

The present invention relates in general to a method of detecting surface defects in mechanical parts, particularly mechanical parts with curved surfaces.

In particular, the invention relates to a method based on the analysis of diffracted light coming from surface defects, this analysis being carried out by observing the changes in the characteristics of a coherent electromagnetic wave in the plane of the spatial frequencies or Fourier plane.

BACKGROUND OF THE INVENTION

The analysis of diffracted light coming from surface defects is a known technique at present in use for detecting and identifying surface defects (cracks, hairline cracks, flaws, cuts, scratches and the like) in mechanical parts. This analysis is normally carried out by illuminating the surface to be examined with even, coherent light and subsequently detecting the spatial intensity distribution of the radiation reflected from the surface subjected to examination.

According to one current implementation, the analysis of the diffracted light coming from the surface defect is carried out by means of a device comprising a first optical transmission system arranged to irradiate the surface to be examined with even, coherent light, and a second optical receiving system, for example a visual display or photoelectric detecting matrix symmetrically disposed relative to the first optical system with respect to the direction normal to the surface to be examined, and arranged to derive information on the spatial intensity distribution of the radiation reflected from the surface under examination.

The theoretical basis of this type of analysis is fully discussed, together with several examples of its possible uses, in chapters 4 and 7 of the work "Introduction to Fourier Optics" by Joseph W. Goodman-McGraw-Hill editions, 1968.

The analysis of diffracted light coming from surface defects, carried out by the processes described previously, is limited in use to checking flat mechanical parts and is not suitable for the qualitative checking of parts with curved surfaces, particularly of parts which have surfaces which do not possess zero curvature in at least one direction (surfaces with double curvature).

In such parts there may be observed a continuous variation, dependent on to the portion examined, in the direction of the normal to the surface, with consequent continuous variation of the direction of propagation of the radiation reflected from the surface under examination. In order to allow the analysis of the diffracted light coming from surface defects in mechanical parts of this type according to the known processess, it is thus necessary to "track" the radiation reflected from the part in space, as well as to ensure the continuously correct positioning of the analysis device at a rigidly predetermined distance from the surface to be checked.

These operating requirements cannot be achieved in practice outside the laboratory and are totally inapplicable to industrial quality control processes, particularly when this control must be effected on all the parts produced.

Moreover, whenever the parts to be inspected have a considerable size, for example motor vehicle bodywork or portions thereof subjected to painting treatments or surface protection, the need to scan the entire surface of the part makes it practically impossible to carry out a qualitative check at a frequency compatible with industrial production times.

OBJECT OF THE INVENTION

The object of the present invention is to provide a method which enables the quality control of the surface finish of mechanical parts with curved surfaces and/or large dimensions to be carried out rapdily and precisely.

SUMMARY OF THE INVENTION

The present invention has as its subject a method of detecting surface defects in mechanical parts, particularly mechanical parts with curved surfaces, by the analysis of diffracted light coming from these surface defects, said method including the steps of:

(a) illuminating, with incoherent light, the surface of the part in which it is desired to detect defects, (b) forming a flat image of the said surface in a transparent photosensitive medium in which the spatial intensity distribution of the incoherent light reflected from the said surface produces a corresponding and proportional spatial distribution of values of the refractive index, (c) illuminating the transparent photosensitive medium with plane polarized coherent light by frame scanning in elementary areas, (d) during the scanning operation, detecting the variations in at least one of the polarization components of the coherent light after the light has traversed the said transparent photosensitive medium, (e) deriving from these variations information regarding any surface defects.

According to the method specified above, the analysis of the diffracted light coming from the surfaces of a mechanical part is effected by examining a flat image of the surface to be checked, thus eliminating the disadvantages described above which occur when the part to be checked has a curved surface, particularly with double curvature.

The invention further relates to apparatus for carrying out the method described above, comprising:

(a) means for illuminating with incoherent light, the surface of the part in which it is desired to detect defects, (b) a spatial light modulator comprising at least one layer of transparent photosensitive material in which a spatial intensity distribution of incoherent light produces a corresponding and proportional spatial distribution of refractive index values, (c) an optical system interposed between the surface of the part in which it is desired to detect defects and the spatial light modulator, the said optical system being arranged to form a flat image of this surface on the said layer of transparent photosensitive material, (d) a source of plane polarized coherent light, (e) means for displacing the said coherent light relative to the spatial light modulator so that the light illuminates the said layer of transparent photosensitive material by frame scanning in elementary areas, (f) detector means arranged, during the scanning operation, to detect variations in at least one of the polarization components of the coherent light after its has traversed the said layer of transparent photosensitive material.

Preferably the apparatus according to the invention further includes electronic processing means connected to the detector means and arranged to derive information relating to any surface defects of the part from the variations in at least one of the polarization components of the coherent light.

THEORETICAL BASIS OF THE INVENTION

The spatial light modulator (spatial light modulator-SLM-or according to another common expression in the art "light valve") is a device of considerable interest for processing optical systems in "real time". It is generally constituted by a flat support on which is disposed a transparent layer of a material which can modify its transmission characteristics for electromagnetic waves, in particular its refractive index, in dependence on the intensity of incoherent light incident on its surface.

The local variation in the value of the refractive index may result from manifestations of different physical phenomena. In a first class of devices, known in the art by the term "PROM-Pockels Readout Optical Modulator-", a layer of photo-conductive material is interposed between two flat transparent electrodes to which a polarizing voltage is applied by means of an external generator. Under these conditions, the variation in conductivity in dependence on the intensity of light incident on the device induces a proportional variation in the refractive index of the material, based on the effect known as the linear electro-optic effect or Pockels effect, which is able to modify the phase characteristics and hence the polarization of coherent light which is propagated within the material.

More particularly, when the light incident on the device has a non-uniform spatial intensity distribution, the corresponding and proportional spatial distribution of refractive index values constitutes an image, generally of the high definition type, of the source of the incoherent light radiation which can even be constituted by a partially reflecting object illuminated by a normal incandescent or fluorescent source. This image may be "read" in a non-destructive manner by causing plane polarized coherent light to fall on the device and detecting the variation in the polarization characteristics of this coherent light after it has traversed the layer of photosensitive material. The "reading" operation may be effected by frame scanning of the layer of photosensitive material in elementary areas (for example lines) according to the criteria currently used in television camera equipment. The spatial light modulator is thus an optical-optical type converter able to convert optical information of an incoherent type into optical information of a coherent type.

The image stored in the device may be cancelled by inverting the polarizing voltage applied to the two transparent electrodes between which the photosensitive layer is interposed. Alternatively, cancelling may be achieved by illuminating the photosensitive layer of material with high intensity, spatially uniform incoherent light (floodlight).

In other spatial light modulators which are different from the PROM described above, the variation in the refractive index is achieved by producing manifestations of the electro-optic effect in materials such as liquid crystals (SLM), photo-dicroic and ferro-electric materials. There are also spatial light modulators in which the image is stored in the form of deformations in the photo-sensitive material layer, thus modifying the length of the optical path, and hence the polarization of the plane polarized coherent light used for the reading operation.

Further information on the theoretical basis and criteria of use of spatial light modulators is contained in the article "Spatial Light Modulators" by D. Casasent-Proceedings of the IEEE, Vol. 65, No. 1, January 1977, pages 143-157, and also in the article "Realtime Spatial Light Modulators" by B. Schneeberger, F. Laeri, T. Tschudi and F. Mast, Optics Communications, Vol. 31, No. 1, October 1979 pages 13-15.

DESCRIPTION OF ONE PREFERRED EMBODIMENT OF THE INVENTION

A preferred embodiment of the invention will now be described with reference to the appended drawings, provided purely by way of non-limiting example, in which:

FIG. 1 is a schematic view of apparatus for carrying out the method according to the invention, and FIG. 2 is a schematic representation of the structure of a spatial light modulator used in the apparatus.

Referring to FIG. 1, S indicates the surface of a part to be checked, for example a part of the bodywork of a motor vehicle.

By 10 is shown a normal light source, for example a tungsten lamp, arranged to illuminate with incoherent light, the surface S of the part to be checked.

An optical system 12 is arranged to form an image of the surface S to be checked on a spatial light modulator 14. Advantageously, the optical system 12 is constituted by an objective, able to form a reduced image of the surface S on the spatial light modulator 14, making it possible and easy to check qualitatively parts with large dimensions. Preferably the objective is of the type with a large depth of field, that is, an objective with a low ratio of the focal length to the diagonal of the image format, such an objective enables the elimination of effects on the accuracy of the check which result from variations in distance from the device of different points on the part itself or of different parts which are to be checked one after another.

The spatial light modulator 14, which is of a type known per se, preferably of the PROM type described above, is formed with the structure illustrated schematically in FIG. 2. This spatial light modulator 14 basically comprises:

(a) a layer 16 of transparent photo-sensitive material in which a spatial intensity distribution of incoherent light induces a corresponding and proportional spatial distribution of values of the refractive index, (b) a first flat electrode 18, transparent to incoherent radiation reflected from the surface S of the part to be checked, (c) a flat dielectric, semi-transparent mirror 20, interposed between the layer of photo-sensitive material 16 and the first flat electrode 18, the reflecting surface of the said dielectric mirror facing the layer of transparent photo-sensitive material 16, (d) a second flat transparent electrode 22 facing the surface of the layer of transparent photo-sensitive material 16 opposite the flat dielectric mirror 20, and (e) a supply unit 24 arranged to apply at least two different voltage levels between the first and the second transparent electrode 18, 22 respectively.

The first voltage level corresponds to the conditions in which, according to the method described above, photo-conductivity characteristics are exhibited by the layer of transparent photo-sensitive material 16 while the second voltage level is that which induces the cancellation of the image stored in this layer of transparent photo-sensitive material 16.

The supply unit 24 controls the memorising and cancelling functions for the image formed on the layer of photo-sensitive material 16, allowing the sequential examination of different spatial light intensity distributions corresponding to images of surfaces of mechanical parts successively taken by the objective 12.

A source of plane polarized coherent light (laser) of known type is indicated 26. The light produced by the source 26 is directed towards the spatial light modulator 14 by means of an optical system which enables this radiation to be displaced relative to the modulator 14. This optical system comprises:

(a) a first mirror 28 arranged to deflect the coherent light produced by the source 26, (b) a second mirror 30 arranged to intercept the light deflected by the first mirror 28 and to deflect it in a direction substantially perpendicular to the surface of the photo-sensitive layer 16 of the spatial light modulator 14, (c) a cylindrical lens 32 located between the first and the second mirrors 28, 30 respectively and having its focus F at the point on the first mirror 28 whereat the light produced by the source 26 is incident, (d) a first drive 34 for oscillating the first mirror 28 about an axis A perpendicular to the line L of the cylindrical lens 32 and to the direction of the light which is emitted by the source 26 and passes through the focus F of the lens 32, and (e) a second drive 36 for oscillating the second mirror 30 about an axis B which intersects the line L of the cylindrical lens 32 and lies in a plane perpendicular to the axis A.

The plane polarized coherent light is deflected by the second mirror 30 towards the spatial light modulator 14 so that the light, after having traversed the second transparent electrode 22, is incident on the layer of transparent photo-sensitive material 16 in a direction substantially perpendicular to the surface of this layer 16.

After having traversed the layer 16, the coherent light is reflected from the semi-transparent mirror 20, passes again through the layer 16 and leaves the spatial light modulator 14. The coherent light leaving the spatial modulator 14 is reflected from a semi-transparent mirror 38, located between the spatial light modulator 14 and the second mirror 30 and is deflected towards a normal optical analyser 40 constituted for example by a polarizer.

By 42 is shown schematically a matrix of photoelectric converters which is disposed in series with the analyser 40 and is arranged to produce at the output of each converter an electric signal indicative of the intensity of the light incident on the converter 42. Between the optical analyser 40 and the matrix of photoelectric converters 42 is interposed a lens 44 arranged to direct the light leaving the analyser 40 onto the matrix of photoelectric converters 42.

An electronic processing circuit indicated by 46 is fed with the signals output from the matrix of photoelectric converters 42. The circuit 46 is arranged to form an array of numerical values corresponding to the spatial intensity distribution of the light incident on the matrix of photoelectric converters 42.

The combination comprising the optical analyser 40, the matrix of photoelectric converters, 42 the lens 44 and the electronic processing circuit 46 constitute a system arranged, during scanning in elementary areas of the layer of transparent photo-sensitive material 16, to detect variations in the light intensity which occur along the direction of one of the polarization components of the coherent radiation after it has traversed this layer of transparent photo-sensitive material 16.

According to a simplified embodiment of the apparatus, not illustrated in the drawings, the matrix of photoelectric counters 42 and the electronic processing circuit 46 may be replaced by an ordinary polished screen adapted to allow the observation of the spatial intensity distribution of the coherent light emerging from the optical analyser 40.

According to the embodiment illustrated in FIG. 1, the apparatus according to the invention further includes a logic control unit 48 connected to the electronic processing circuit 46, to the drives 34 and 36, and to the supply unit 24 for the spatial light modulator 14. This logic control unit 48 is preferably constituted by a micro-processor system which is able to follow the operations of the electronic processing circuit 46.

DESCRIPTION OF THE OPERATION OF THE DEVICE

After the surface S to be checked has been correctly framed and brought into focus by the objective 12, the logic control unit 48 controls the supply unit 24 of the spatial light modulator 14 to allow storage of the image of the surface S to be checked in the layer of transparent photo-sensitive material 16. Simultaneously, or after a predetermined period of time, the logic control unit 48 activates the drives 34 and 36 to oscillate the first and second mirrors 28, 30 respectively, starting the scanning in elementary areas of the layer of transparent photo-sensitive material 16.

When, during the scanning operation, the coherent light passes through elementary areas of the layer of transparent photo-sensitive material 16 corresponding to portions of the surface to be checked which are free from defects (or, possibly corresponding to surfaces of a sample part free from defects), the light incident on the matrix of photoelectric converters 42 has a spatial intensity distribution which is taken as a reference. For example, when the surfaces are subjected to a painting treatment (parts of vehicle bodywork), the reference distribution is comparable to a luminous spot located in the centre of the photoelectric converter matrix 42, which corresponds to the origin of the plane of the spatial frequencies (Fourier plane) represented by the surface of the matrix of photoelectric converters 42.

The presence of a defect on the surface S to be checked produces a variation in the spatial distribution of the intensity of the light incident on the matrix of photoelectric converters 42, giving this distribution an elongate or irregular geometry, or at least a geometry different from that taken as the reference. This variation is detected by the electronic processing circuit 46 and signalled to the logic control unit 48 which, being connected to the scanning means (mirrors 28, 30 and drives 34, 36) identifies the elementary area of the layer of photo-sensitive material 16 and, consequently, the portion of the surface S to be checked on which the presence of a defect has been found, emitting a corresponding alarm signal.

The electronic processing circuit 46 is also able to identify, on the basis of algorithms of known type, the type of defect (score, hole, crack etc.) found, from the particular spatial intensity distribution of the light incident on the matrix of photoelectric converters 42 in the presence of the defect.

At the end of the scanning operation, the logic control unit 48, through the supply unit 24, is arranged to cancel the image stored in the spatial light modulator 14, and simultaneously signal its availability to effect a further checking cycle.

The next checking cycle may be effected on a mechanical part different from that checked previously, or on another portion of the part checked during the preceding cycle whenever, as in the case of the quality control of a vehicle body subjected to painting, the dimensions of the part to be checked are considerable so that the part cannot be brought completely within the field of view of the objective 12.

In this case the apparatus may usefully be connected to an automatic arrangement for relatively positioning the apparatus itself with respect to the part to be checked, whereby to render the carrying through of the checking operation completely automatic.

Naturally, the principle of the invention remaining the same, the details of construction and the embodiments of the apparatus may be varied widely with respect to that described and illustrated, without thereby departing from the scope of the present invention.

I claim:

1. A method of detecting surface defects in mechanical parts by analysis of diffracted light coming from these surface defects, said method comprising the steps of:
    (a) illuminating, with incoherent light, the surface of the part in which it is desired to detect defects,
    (b) forming a flat image of this surface in a transparent photo-sensitive medium in which the spatial intensity distribution of the incoherent light reflected from the said surface produces a corresponding and proportional spatial distribution of the values of refractive index of said medium,
    (c) illuminating the transparent photo-sensitive medium with plane polarized coherent light by frame scanning in elementary areas,
    (d) during the scanning operation, detecting variations in at least one of the polarization components of the coherent light after the latter has traversed the said transparent photo-sensitive medium, and
    (e) deriving from these variations, information on possible defects in the surface under examination.

2. Apparatus for detecting surface defects in mechanical parts by analysis of diffracted light coming from these surface defects, said apparatus comprising:
    (a) means for illuminating, with incoherent light, the surface of the part in which it is desired to detect defects,
    (b) a spatial light modulator comprising at least one layer of transparent photo-sensitive material in which a spatial intensity distribution of incoherent light produces a corresponding and proportional spatial distribution of the values of refractive index,
    (c) an optical system interposed between the surface of the part in which it is desired to detect defects and the spatial light modulator, the said optical system being arranged to form a flat image of this surface on the said layer of transparent photo-sensitive material,
    (d) a source of plane polarized coherent light,
    (e) scanning means for displacing the said coherent light relative to the spatial light modulator so that this light illuminates the said layer of transparent photo-sensitive material by scanning in elementary areas, and
    (f) detector means arranged, during the scanning operation, to detect variations in at least one of the polarization components of the coherent light after this light has traversed the said layer of transparent photo-sensitive material.

3. Apparatus according to claim 2, further including electronic processing means connected to the detector means and arranged to derive information on any surface defect of the surface under examination from the said variations in at least one of the polarization components of the coherent light.

4. Apparatus according to claim 2, wherein the spatial light modulator provided with the said layer of transparent photo-sensitive material, comprises:
    (a) a first flat electrode transparent to the incoherent light reflected from the surface under examination,
    (b) a flat dielectric, semi-transparent mirror interposed between the layer of transparent photosensitive material and the first flat electrode, the reflecting surface of the said mirror facing the said layer of transparent photo-sensitive material,
    (c) a second flat electrode transparent to the coherent light and facing the surface of the layer of transparent photo-sensitive material opposite the flat dielectric mirror, and
    (d) a supply unit arranged to apply at least two different voltage levels between the first and second transparent electrodes.

5. Apparatus according to claim 2, wherein the said optical system includes an objective with a large depth of field.

6. Apparatus according to claim 2, wherein the said scanning means comprise:
    (a) a first mirror arranged to deflect the light produced by the coherent light source,
    (b) a second mirror arranged to deflect the light deflected by the first mirror in a direction substantially normal to the surface of the layer of transparent photosensitive material of the spatial light modulator,
    (c) a cylindrical lens interposed between the first and second mirrors with its focus at the point on the first mirror lit by the light coming from the coherent light source,
    (d) first drive means for oscillating the first mirror about an axis perpendicular to the axis of the cylindrical lens and to the incidence direction of the coherent light passing through the focus of this cylindrical lens, and
    (e) second drive means for oscillating the second mirror about an axis which intersects the axis of the cylindrical lens and which lies in a plane perpendicular to the axis about which the said first mirror is oscillated.

7. Apparatus according to claim 3, wherein the said detector means comprise:
    (a) an optical analyser,
    (b) a first optical system arranged to deflect the coherent light leaving the spatial modulator towards the said optical analyser,
    (c) a matrix of photoelectric converters arranged to produce at the output of each converter an electrical signal indicative of the value of the intensity of the light incident on that converter, and (d) a second optical system arranged to direct the light leaving the optical analyser onto the matrix of photoelectric converters.

8. Apparatus according to claim 7, wherein the said optical analyser is a polarizer.

9. Apparatus according to claim 7 or claim 8, wherein the said first optical system of the detector means is constituted by a semi-transparent mirror.

10. Apparatus according to claim 7, wherein the said detector means further comprise an electronic circuit fed with the signals output from the matrix of photoelectric converters and arranged to form an array of numerical values corresponding to the spatial intensity distribution of the light incident on the matrix of photoelectric converters.

11. Apparatus according to claim 10, wherein said detector means further comprises a logic control unit connected to the electronic circuit and the said scanning means.

* * * * *